(12) United States Patent
Van Der Sluis et al.

(10) Patent No.: US 9,572,944 B2
(45) Date of Patent: Feb. 21, 2017

(54) NEBULIZER, A CONTROL UNIT FOR CONTROLLING THE SAME, A NEBULIZING ELEMENT AND A METHOD OF OPERATING A NEBULIZER

(75) Inventors: Paul Van Der Sluis, Eindhoven (NL); Alwin Rogier Martijn Verschueren, 'S-Hertogenbosch (NL); Markus Hijlkema, Eindhoven (NL); Jeroen Herman Lammers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 138 days.

(21) Appl. No.: 14/344,724

(22) PCT Filed: Aug. 30, 2012

(86) PCT No.: PCT/IB2012/054453
§ 371 (c)(1),
(2), (4) Date: Mar. 13, 2014

(87) PCT Pub. No.: WO2013/041995
PCT Pub. Date: Mar. 28, 2013

(65) Prior Publication Data
US 2014/0346245 A1 Nov. 27, 2014

Related U.S. Application Data

(60) Provisional application No. 61/536,123, filed on Sep. 19, 2011.

(51) Int. Cl.
*B05B 1/08* (2006.01)
*A61M 11/00* (2006.01)
(Continued)

(52) U.S. Cl.
CPC .......... *A61M 11/001* (2014.02); *A61M 11/005* (2013.01); *A61M 15/0085* (2013.01);
(Continued)

(58) Field of Classification Search
CPC .................................................. A61M 11/001
(Continued)

(56) References Cited

U.S. PATENT DOCUMENTS 5,152,456 A 10/1992 Ross
5,261,601 A * 11/1993 Ross ................. A61M 15/0085
128/200.16
(Continued)

FOREIGN PATENT DOCUMENTS

CN 1054916 A 10/1991
CN 1788806 A 6/2006
(Continued)

OTHER PUBLICATIONS

Lin et al, "An Ultrasonic Aerosol Therapy Nebulizer Using Electroformed Palladium-Nickel Alloy Nozzle Plates", SNES. Acutators SA: Phys., 2011, pp. 1-7.

Primary Examiner — Ryan Reis
Assistant Examiner — Adam J Rogers
(74) Attorney, Agent, or Firm — Michael W. Haas (57) ABSTRACT

There is provided a control unit for controlling the operation of a nebulizer, the nebulizer comprising a reservoir chamber for storing a liquid to be nebulised, an actuator, and a nebulizing element comprising a plurality of nozzles arranged to nebulize the liquid upon operation of the actuator; wherein the control unit is configured to obtain an indication of the size of the nozzles in the nebulizing element; and control the operation of the actuator based on the obtained indication to provide nebulised liquid at a required output rate and/or with droplets of a required size.

5 Claims, 4 Drawing Sheets (51) Int. Cl.
*A61M 15/00* (2006.01)
*B05B 12/08* (2006.01)
*B05B 17/00* (2006.01)

(52) U.S. Cl.
CPC .......... *B05B 12/08* (2013.01); *B05B 17/0638* (2013.01); *B05B 17/0646* (2013.01); *A61M 2205/50* (2013.01); *A61M 2205/60* (2013.01); *A61M 2205/6018* (2013.01); *A61M 2205/6054* (2013.01)

(58) Field of Classification Search
USPC ........ 239/102.1; 128/202.21, 203.12–203.29
See application file for complete search history.

(56) References Cited

U.S. PATENT DOCUMENTS

| | | | |
|---|---|---|---|
| 5,422,664 A | 6/1995 | Stephany | |
| 5,455,606 A | 10/1995 | Keeling et al. | |
| 7,225,807 B2 * | 6/2007 | Papania | A61M 11/005 128/200.14 |
| 7,785,277 B2 | 8/2010 | Babaev et al. | |
| 8,382,008 B1 * | 2/2013 | Ricciardi | A61L 2/22 128/200.16 |
| 2006/0146327 A1 | 7/2006 | Wang et al. | |
| 2007/0074722 A1 * | 4/2007 | Giroux | A61M 11/06 128/203.15 |
| 2008/0142010 A1 * | 6/2008 | Weaver | A61M 11/041 128/203.26 |
| 2008/0271732 A1 * | 11/2008 | Weaver | A61M 11/041 128/200.14 |
| 2009/0288659 A1 * | 11/2009 | Haveri | A61M 16/18 128/203.14 |
| 2009/0324815 A1 | 12/2009 | Nielsen et al. | |
| 2010/0163573 A1 | 7/2010 | Wegelin et al. | |
| 2010/0163575 A1 | 7/2010 | Huang | |
| 2011/0226868 A1 * | 9/2011 | Modlin | A01M 1/205 239/102.1 |
| 2012/0146251 A1 * | 6/2012 | Heine | A61M 16/16 261/128 |
| 2013/0079733 A1 * | 3/2013 | Burt | B05B 7/0012 604/290 |
| 2014/0047714 A1 | 2/2014 | Van Der Sluis et al. | |

FOREIGN PATENT DOCUMENTS

| | | |
|---|---|---|
| EP | 0775587 | 7/2000 |
| EP | 0931663 | 11/2004 |
| JP | S586263 A | 1/1983 |
| JP | 2004249208 A | 9/2004 |
| JP | 2008271732 A | 11/2008 |
| JP | 2011254686 A | 12/2011 |
| WO | 2012147009 A1 | 11/2012 |

* cited by examiner

```
 ┌─────────────────────────────────────────┐
 │ Read information on nozzle size         │──101
 │ from RFID tag associated with the       │
 │ nozzle plate in the nebuliser           │
 └─────────────────────────────────────────┘
                    │
                    ▼
 ┌─────────────────────────────────────────┐
 │ Adjust of set the pulse length of       │──103
 │ the piezoelectric element based on      │
 │ the nozzle size information             │
 └─────────────────────────────────────────┘
```

FIG. 7

NEBULIZER, A CONTROL UNIT FOR CONTROLLING THE SAME, A NEBULIZING ELEMENT AND A METHOD OF OPERATING A NEBULIZER

CROSS-REFERENCE TO PRIOR APPLICATIONS

This application is the U.S. National Phase application under 35 U.S.C. §371 of International Application Ser. No. PCT/IB2012/054453, filed on AUG. 30, 2012, which claims the benefit of U.S. application Ser. No. 61/536,123, filed on SEP. 19, 2011. These applications are hereby incorporated by reference herein.

TECHNICAL FIELD OF THE INVENTION

The invention relates to a nebulizer that nebulizers a liquid stored therein into fine droplets, for example for inhalation by a user, and in particular relates to a method of operating a nebulizer to achieve a desired flow rate and/or droplet size and a control unit for a nebulizer and nebulizing element configured to implement the method.

BACKGROUND TO THE INVENTION

Nebulizers, or atomizers as they are sometimes called, are devices that generate a fine spray or aerosol from a liquid. A particularly useful application for nebulizers is to provide a fine spray containing a dissolved or a suspended particulate drug for administration to a patient by inhalation.

Piezo-mesh based nebulizers are commonly used to generate aerosols in such drug delivery apparatus, whereby for instance a piezoelectric element vibrates a nozzle plate (otherwise referred to as a mesh) to produce the fine aerosol spray. In some nebulizers the piezoelectric element is bonded to a nozzle plate element, whereas in other nebulizers the nozzle plate element is separate from (i.e. not in contact with) the piezoelectric element (sometimes referred to as piezo-cavity-mesh based nebulizers). An advantage of having the nozzle plate element separate from the piezoelectric element is that the nozzle plate element can be removed from the nebulizer and cleaned or entirely replaced after a certain amount of use.

In order for a particular medicine to be therapeutically effective when inhaled, the aerosol droplet size of the medicine must be within a narrow therapeutic range. As the generation of droplets is accomplished by pressing the liquid through the holes (nozzles) in the nozzle plate, and the size of the droplets is determined, in part, by the size of the nozzles in the nozzle plate, ideally each nozzle in the nozzle plate should be of the required size. Typically, it is desirable for the nozzles to have a diameter of 2.5 µm with a tolerance of +/−0.25 µm. There can be of the order of 5000 nozzles in a typical nozzle plate.

Due to limitations in the process of manufacturing nozzle plates, it is difficult to consistently produce nozzle plates with nozzles at the desired size (or within the required tolerance) and with the nozzles having a consistent size across each plate, and thus the production yield of the manufacturing process is quite low, sometimes around 10%.

Furthermore, it has been found that even a small variation in nozzle size (for example within the normally accepted tolerance range for nozzle size of +/−0.25 µm) leads to a large variation in the output rate (flow rate) of the nebulizer. Since the dosage regime for a particular medicine may need to be precisely controlled, this variation in flow rate is unacceptable. In particular, to achieve a variation in flow rate of just 25% from a desired flow rate, it has been found that the maximum permissible variation in nozzle size from the desired size is +/−0.05 µm. However, applying this smaller tolerance range to the conventional manufacturing process would further reduce the production yield. As the nozzle plate is a consumable element of the nebulizer (i.e. it can often be replaced), this is highly undesirable.

Therefore, there is a need for an improved way of operating a nebulizer to achieve a desired flow rate and/or droplet size, despite the variation in nozzle size across different nozzle plates that could be used in the nebulizer.

SUMMARY OF THE INVENTION

According to a first aspect of the invention, there is provided a control unit for controlling the operation of a nebulizer, the nebulizer comprising a reservoir chamber for storing a liquid to be nebulized, an actuator, and a nebulizing element comprising a plurality of nozzles arranged to nebulize the liquid upon operation of the actuator; wherein the control unit is configured to obtain an indication of the size of the nozzles in the nebulizing element; and control the operation of the actuator based on the obtained indication to provide nebulized liquid at a required output rate and/or with droplets of a required size.

In a preferred embodiment, the control unit is configured to operate the actuator in a pulsed mode of operation in which the actuator is periodically operated at a frequency f for a number of cycles followed by a period of rest, and wherein the control unit is configured to operate the actuator at a first number of cycles when the nozzles are a first size and a second number of cycles when the nozzles are a second size, the second number of cycles being higher than the first number of cycles and the second size being less than the first size.

In other preferred embodiments, the control unit is configured to adjust or set one or more operating parameters of the nebulizer based on the obtained indication to provide the nebulised liquid at the required output rate and/or with the required droplet size, the one or more operating parameters being selected from (i) the peak voltage of a control signal for the actuator; (ii) the length of an active portion and/or a rest portion of a periodic control signal for the actuator, the active portion of the control signal causing the actuator to operate to nebulize liquid; (iii) the frequency of a control signal for the actuator; and/or (iv) the distance between the actuator and the nebulizing element.

In preferred embodiments, the control unit comprises a reader for reading data stored in an electronically-readable tag associated with the nebulizing element, the data comprising the indication of the size of the nozzles in the nebulizing element.

In some embodiments, the control unit further comprises a memory that is configured to store a look-up table of nozzle sizes and values for at least one operating parameter for the actuator, and wherein the control unit is configured to use the look-up table and obtained indication to determine the value for at least one operating parameter to use to operate the actuator and to provide the nebulised liquid at the required output rate and/or with the required droplet size.

Preferably, the control unit is configured to obtain the indication of the size of the nozzles in the nebulizing element upon installation of the nebulizing element in the nebulizer or upon activation of the nebulizer.

According to a second aspect of the invention, there is provided a nebulizing element for use in a nebulizer, the nebulizing element comprising a plate comprising a plurality of nozzles; and an indication of the size of the nozzles in the plate.

In a preferred embodiment, the nebulizing element further comprises an electronically-readable tag, the indication of the size of the nozzles in the plate being stored in the electronically-readable tag.

According to a third aspect of the invention, there is provided a nebulizer, comprising a reservoir chamber for storing a liquid to be nebulised; an actuator that is configured to vibrate in order to nebulize the liquid stored in the reservoir chamber; and a control unit as described above.

Preferably, the nebulizer further comprises a nebulizing element as described above positioned in the reservoir chamber.

According to a fourth aspect of the invention, there is provided a method of operating a nebulizer, the nebulizer comprising a reservoir chamber for storing a liquid to be nebulised, an actuator, and a nebulizing element comprising a plurality of nozzles arranged to nebulize the liquid upon operation of the actuator; the method comprising obtaining an indication of the size of the nozzles in the nebulizing element; and controlling the operation of the actuator based on the obtained indication to provide nebulised liquid at a required output rate and/or with droplets of a required size.

In a preferred embodiment, the step of controlling the operation of the actuator comprises operating the actuator in a pulsed mode of operation in which the actuator is periodically operated at a frequency f for a number of cycles followed by a period of rest and wherein the step of controlling the operation of the actuator comprises operating the actuator at a first number of cycles when the nozzles are a first size and operating the actuator at a second number of cycles when the nozzles are a second size, the second number of cycles being higher than the first number of cycles and the second size being less than the first size.

In alternative preferred embodiments, the step of controlling the operation of the actuator comprises adjusting or setting one or more operating parameters of the nebulizer based on the obtained indication to provide the nebulised liquid at the required output rate and/or with the required droplet size, the one or more operating parameters being selected from (i) the peak voltage of a control signal for the actuator; (ii) the length of an active portion and/or a rest portion of a periodic control signal for the actuator, the active portion of the control signal causing the actuator to operate to nebulize liquid; (iii) the frequency of a control signal for the actuator; and/or (iv) the distance between the actuator and the nebulizing element.

Preferably, the step of obtaining an indication comprises reading data stored in an electronically-readable tag associated with the nebulizing element, the data comprising the indication of the size of the nozzles in the nebulizing element.

In some embodiments, the step of controlling the operation of the actuator comprises using the obtained indication and a look-up table of nozzle sizes and values for at least one operating parameter for the actuator to determine the value for the at least one operating parameter to use to operate the actuator to provide the nebulised liquid at the required output rate and/or with the required droplet size.

Preferably, the step of obtaining comprises obtaining the indication of the size of the nozzles in the nebulizing element upon installation of the nebulizing element in the nebulizer or upon activation of the nebulizer.

According to a fifth aspect of the invention, there is provided a computer program product comprising a computer readable medium having computer program code embodied therein, the computer program code comprising code that, when executed by a computer or processor, is configured to cause the computer or processor to perform the steps in the method as described above.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Although the invention is primarily described herein as being for addressing the problems associated with variations in the size of nozzles in nozzle plates that can be used in a nebulizer, the invention can alternatively or additionally be used to adjust the output flow rate and/or droplet size provided by a particular nozzle plate (regardless of whether the nozzles in the nozzle plate are of the correct size). This is particularly useful where different medications or treatment regimens require different flow rates, and it is desirable to be able to produce those output flow rates from a single nozzle plate. Likewise, where the nebulizer is being used by a small child, it is desirable to be able to generate droplets of a smaller size than normal without having to change the nozzle plate in the nebulizer.

Figure 1:
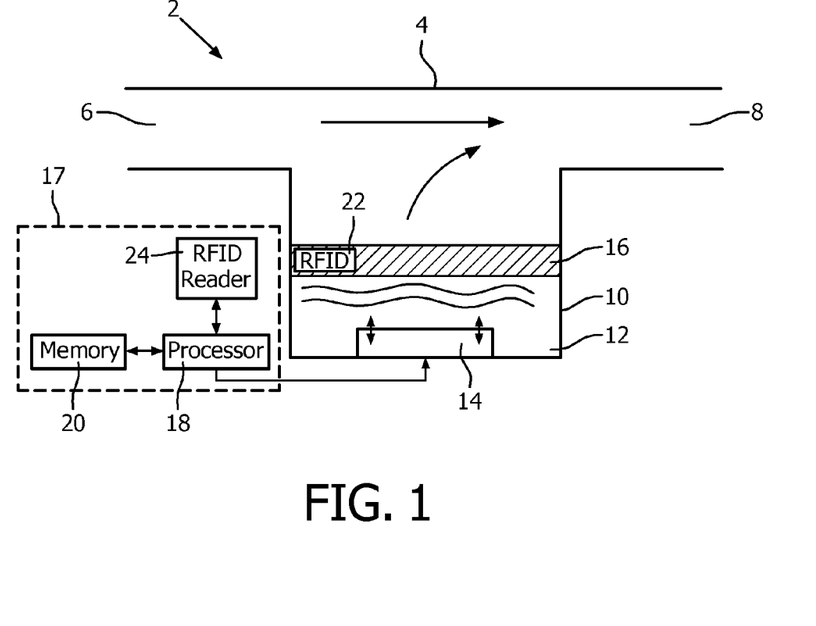
FIG. 1 is a block diagram of a nebulizer comprising a nozzle plate according to an embodiment of the invention.
Figure 2:
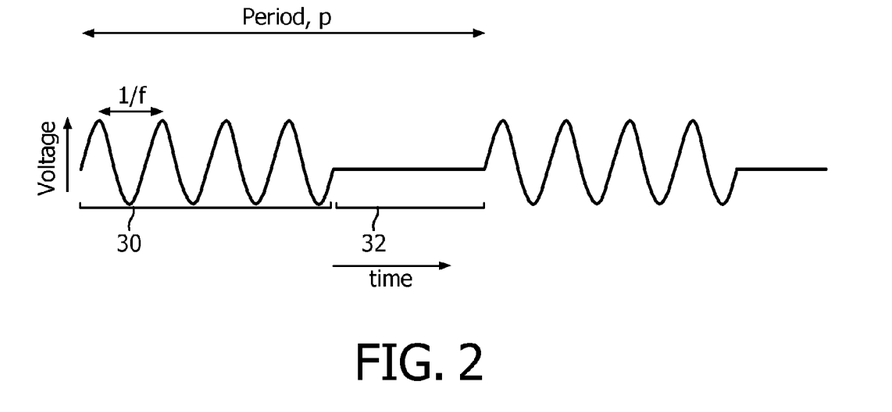
FIG. 2 is a diagram illustrating an exemplary signal for controlling an actuator in a nebulizer.
Figure 3:
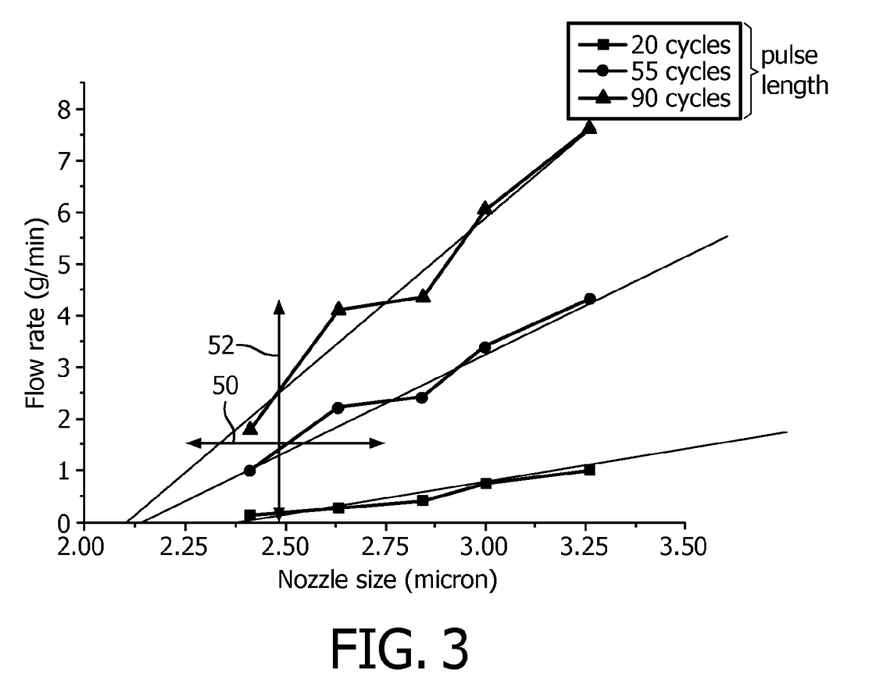
FIG. 3 is a graph illustrating the variation in output (flow) rate with changes in nozzle size.

FIG. 1 shows an exemplary nebulizer 2. The nebulizer 2 comprises a body 4 having an inlet 6 and an outlet 8 arranged so that when a user of the nebulizer 2 inhales through the outlet 8, air is drawn into and through the nebulizer 2 via the inlet 6 and outlet 8 and into the user's body. The outlet 8 is typically provided in the form of a mouthpiece or a facial or nasal mask or in a form that is suitable for connection to a separate replaceable mouthpiece or facial or nasal mask.

The nebulizer 2 comprises a reservoir chamber 10 between the inlet 6 and outlet 8 for storing a liquid 12, for example a medication or drug, to be nebulised (i.e. to be turned into a fine mist or spray). The nebulizer 2 is configured such that fine droplets of the nebulised liquid 12 combine with the air drawn through the nebulizer 2 when the user inhales to deliver a dose of the medication or drug to the user.

An actuator 14 is provided for agitating or vibrating the liquid 12 stored in the reservoir chamber 10. In the embodiments of the invention that are described further below, the actuator 14 is provided in the form of a piezoelectric element. However, those skilled in the art of nebulizers will appreciate that other forms of actuator 14 can be used in nebulizers according to the invention. It will also be appreciated that a piezoelectric element 14 can be covered with a plastic or metal cover layer to avoid direct contact between the piezoelectric element and the liquid 12.

A nozzle plate 16 is provided in the reservoir chamber 10 for nebulizing the liquid 12 when the liquid 12 is vibrated by the actuator 14. The nozzle plate 16 is typically in the form of a mesh or membrane having a plurality of small holes or nozzles through which small amounts of the liquid can pass. The size (diameter) of the nozzles in the nozzle plate 16 determines, among other things, the size of the droplets of liquid produced when the nebulizer 2 is activated. The size of the droplets of liquid produced can be measured in terms of the mass mean diameter (MMD). The nozzle plate 16 is removable from the nebulizer 2 so that it can be cleaned or completely replaced, as required.

In the illustrated embodiment, the actuator 14 is separate from the nozzle plate 16 and is positioned at, or proximate to, the bottom of the reservoir chamber 10 in order to agitate the liquid 12. However, in alternative embodiments the actuator 14 can be in contact with or integral with the nozzle plate 16 and can vibrate the nozzle plate 16 in order to nebulize the liquid 12.

In use, the liquid 12 fills the reservoir chamber 10 up to the height of the nozzle plate 16. It will be appreciated that the liquid 12 in the reservoir chamber 10 will be depleted as the nebulizer 2 is operated, and more liquid 12 must be added to the reservoir chamber 10 to maintain the liquid 12 at the required height for the nebulizer 2 to continue operating. Therefore, the nebulizer 2 may comprise, or be coupled to, a further chamber (not shown in FIG. 1) that stores liquid for replenishing the liquid 12 in the reservoir chamber 10. The liquid from the further chamber may flow into the reservoir chamber 10 due to the action of gravity and/or capillary filling.

The nebulizer 2 further comprises a control unit 17 that controls the operation of the nebulizer 2. The control unit 17 comprises a processor 18 that is electrically connected to the actuator 14. The processor 18 outputs control signals to the actuator 14 that cause the actuator 14 to operate and nebulize the liquid 12 as described further below.

A memory 20 is also provided that can store operating parameters and/or program instructions for use by the processor 18 during operation of the nebulizer 2. The operating parameters may, for example, relate to the dosage regime to be provided by the nebulizer 2, such as the required treatment time and/or medication flow rate.

In the illustrated embodiment, the control signals output to the actuator 14 by the processor 18 cause the actuator 14 to operate in a 'pulsed' operation mode. In this mode, the control signal causes the actuator 14 to actuate at a frequency f for a particular number of cycles in a row, and then causes the actuator 14 to rest for a further number of cycles. This actuated and non-actuated operation is repeated during the operation of the nebulizer 2. In one embodiment, frequency f is 1 MHz, although it will be appreciated that other frequencies may be used.

An exemplary control signal for this 'pulsed' operation is shown in FIG. 2 where it can be seen that the control signal comprises an active portion 30 (sometimes referred to herein as the 'pulse') comprising four cycles of actuation at frequency f, followed by a rest period 32 in which the actuator 14 is not actuated. The length of the active portion 30, referred to as the 'pulse length' or 'number of cycles' herein (and which can be defined as the number of cycles of the signal at frequency f that are in the active portion 30), and non-actuated (rest) portion 32 is the period, p.

Referring now to FIG. 3, a solution provided by the invention will be explained in more detail. FIG. 3 shows the output (flow) rate in grams per minute (g/min) obtained for five nozzle plates, each having a different average nozzle size (2.41 μm, 2.63 μm, 2.83 μm, 3 μm and 3.25 μm) at three different pulse lengths of operation for an actuator 14.

By grouping the flow rates by pulse length, it can be seen that, for a given pulse length, the flow rate increases generally linearly as nozzle size increases. In particular, within the acceptable range of nozzle sizes given above, i.e. 2.5 μm+/−0.25 μm, indicated by arrow 50, the output rate varies from 0 to around 4.5 g/min with increasing pulse length, indicated by arrow 52. In other words, by varying the ratio of on and off cycles (i.e. the ratio of the number of cycles in the active portion 30 to the number of cycles in the rest portion 32), the output flow rate of the nebulizer 2 can be adjusted.

If we assume that an output rate of 1.5 g/min is desired, a pulse length of 55 cycles will provide the required flow rate when the average nozzle size is 2.5 μm. However, when the average nozzle size is just under 2.75 μm (so still within the acceptable tolerance for nozzle size), a pulse length of 55 cycles results in an output rate of around 2.4 g/min, which is too high. Therefore, in this case, reducing the pulse length to around 27 cycles (i.e. part way between the 20 cycles and 55 cycles lines illustrated in FIG. 2) will result in the required flow rate of 1.5 g/min. Similarly, when the average nozzle size is around 2.34 μm, a pulse length of 55 cycles results in an output rate of around 1.0 g/min, which is too low. Therefore, in this case, increasing the pulse length to around 90 cycles will result in the required flow rate of 1.5 g/min.

FIG. 4 is another graph illustrating how the flow rate in g/min is affected by the number of cycles in a pulse. This particular mesh has an average nozzle size of 2.36 micron. It can be seen in this Figure that the flow rate increases generally linearly with the number of cycles in a pulse.

Thus, in accordance with one preferred embodiment of the invention, the control unit 17 is configured to control the nebulizer 2 such that the number of cycles in a pulse (i.e. the pulse length) for the actuator 14 is varied or set based on the size or average size of the nozzles in the nozzle plate 16 present in the nebulizer 2, in order to provide a required output flow rate. In general, the larger the size of the nozzles in the nozzle plate 16, the lower the number of cycles in a pulse for the actuator 14, and vice versa.

FIG. 5 shows two exemplary control signals that could be used in accordance with this embodiment of the invention. The upper signal corresponds to that shown in FIG. 2 which has a pulse length of 4 (i.e. 4 cycles of the signal at frequency f), and may be used for a nozzle plate 16 that has relatively small nozzles, and the lower signal has a pulse length of 2 (i.e. 2 cycles of the signal at frequency f) that will be used for a nozzle plate 16 having larger nozzles.

As the nozzle plate 16 is a replaceable element of the nebulizer 2 and the average size of the nozzles will vary across different nozzle plates 16, it is necessary to determine the average size of the nozzles for the nozzle plate 16 that is currently in use in the nebulizer 2 so that the control signal for operating the actuator 14 can be appropriately set.

Thus, during or after manufacture of a particular nozzle plate 16, the size of the nozzles in the nozzle plate 16 can be measured, and this information recorded for use by the nebulizer 2. This information can then be automatically read by or manually input into the nebulizer 2 prior to operation, and the information used to set the number of cycles in a pulse for the actuator 14 to obtain the desired output flow rate. The information can comprise the average size of the nozzles in the nozzle plate 16, for example a mean, median or mode of the measured nozzle sizes or the size range of the nozzles in the nozzle plate 16.

One technique for measuring the size, average size, or variation in size of the nozzles in a nozzle plate 16 is described in European patent application no. 11163885.4 (now U.S. Published Application No. 20140047714A1) entitled "Nozzle plate fabrication" in the name of Koninklijke Philips Electronics N.V., the content of which is hereby incorporated by reference. Briefly, that technique comprises illuminating a nozzle plate with light, detecting the light transmitted through a plurality of nozzles in the nozzle plate; and analyzing the detected light to determine a variation in the size of the nozzles across the nozzle plate.

The results of this, or any other suitable technique for measuring nozzle size (which will be apparent to those skilled in the art) can be recorded in or on the nozzle plate 16 in a number of different ways.

For example, in one embodiment, the average size of the nozzles in a nozzle plate 16 can be printed onto the nozzle plate 16. When a user installs the nozzle plate 16 into the nebulizer 2, they can read the printed average nozzle size and input this into the nebulizer 2 via a user interface (not shown in FIG. 1). Alternatively, the nebulizer 2 can be provided with some means (for example a camera or other optical sensor in conjunction with optical character recognition software) for reading the printed average size from the nozzle plate 16.

In an alternative embodiment, rather than printing the actual average size of the nozzles onto the nozzle plate 16, the average size can be presented in a simplified format that is easier for a user to input into the nebulizer 2 or for the nebulizer 2 to automatically read. This simplified format could comprise a single digit or letter that represents a particular range of average nozzle sizes (for example the number 1 could represent an average nozzle size of 2-2.1 μm, the number 2 could represent an average nozzle size of 2.1-2.2 μm, and so on).

However, in a preferred embodiment of the invention, information on the average size of the nozzles in the nozzle plate 16 is stored in an electronically-readable tag, such as a Radio-Frequency Identification (RFID) tag, that is part of the nozzle plate 16. The information could be stored in terms of the actual average size of the nozzles or in terms of the simplified format described above. Thus, referring again to FIG. 1, the nozzle plate 16 is provided with an RFID tag 22 that stores the nozzle size indication, and the control unit 17 further comprises an RFID tag reader 24 that is connected to the processor 18.

In another embodiment of the invention, the desired flow rate may depend on the particular medication to be administered. In this case, a nozzle plate 16 can be supplied with the medication, and the information on the average size of the nozzles in the nozzle plate 16 described above can be supplemented by information on the required flow rate. This information can also be read by or input to the nebulizer 2 and used to adjust the operation of the nebulizer 2 accordingly.

Figure 6:
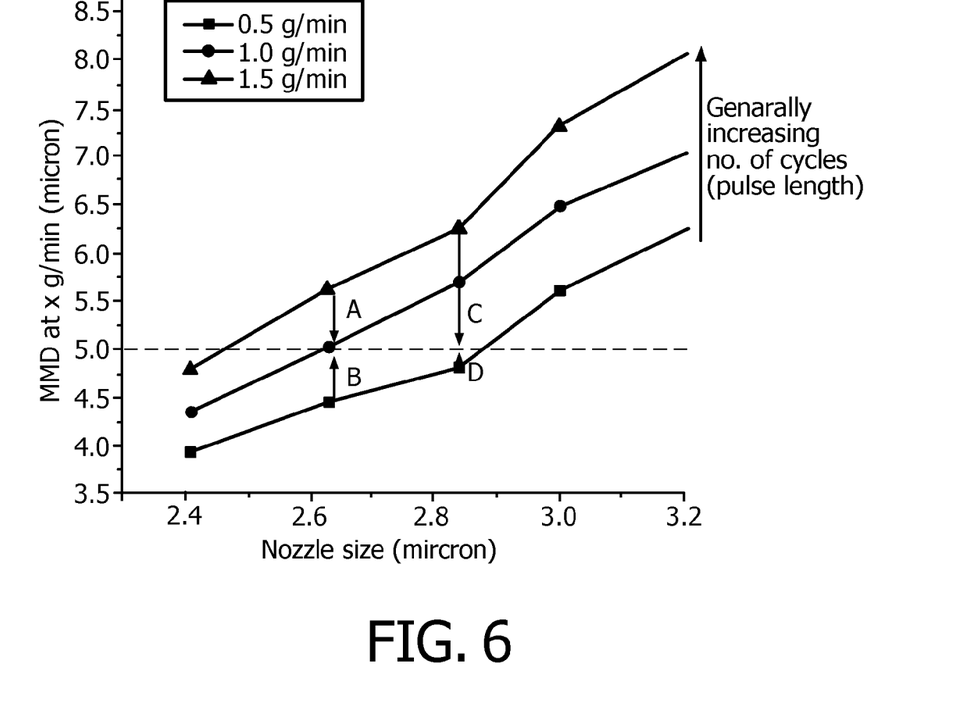
FIG. 6 is a graph illustrating a relationship between nozzle size and the mass mean diameter of generated droplets for different output flow rates.

FIG. 6 is a graph that shows a relationship between nozzle size (measured in microns) and mass mean diameter (MMD—also measured in microns) for different flow rates. The graph shows the droplet size obtained for four different nozzle plates 16 having nozzle sizes of 2.41 microns, 2.63 microns, 2.83 microns and 3.0 microns respectively, that are operated with three different sets of pulse lengths in order to obtain flow rates of 0.5 g/min, 1.0 g/min and 1.5 g/min. It can be seen that, for an exemplary target droplet size (MMD) of 5 microns with a nozzle plate 16 having an average nozzle size of 2.63 microns, it is necessary to use a control signal with the number of cycles (pulse length) required to achieve an output flow rate of 1 g/min.

If the droplet size is too big (for example 5.6 microns), the number of cycles can be reduced in order to reduce the size of the droplets down to around 5 microns (as indicated by arrow A in FIG. 6). Likewise, if the droplet size is too small (for example 4.4 microns), the number of cycles can be increased in order to increase the size of the droplets (as indicated by arrow B in FIG. 6).

For a nozzle plate having a larger average nozzle size (for example 2.83 microns), the target droplet size of 5 microns can be achieved by adjusting the control signal to include a lower number of cycles than the control signal for the nozzle plate with the average nozzle size of 2.63 microns (as indicated by arrows C and D in FIG. 6). It will be seen from FIG. 6 that the required droplet size for this nozzle plate will result in a lower flow rate.

It will be appreciated that, generally speaking, adapting the control signal to set the MMD of the generated droplets to a desired value will result in the output rate of the nebulizer 2 being adjusted too. However, after setting the number of cycles to a certain value in order to achieve a required droplet size, it is possible to further adjust the control signal or other parameters of the nebulizer 2 in order to adjust the flow rate.

For example, if the nozzle plate 16 has an average nozzle size of 2.63 microns and it is desirable to produce droplets having an MMD of 5 microns, the number of cycles is set as shown in FIG. 6, and this results in a flow rate of 1 g/min. If it is desired to increase the flow rate, then two consecutive steps should be taken. First the period of the control signal can be reduced while keeping the ratio between the active and inactive periods substantially constant). This results in more or less the same flow rate, while the MMD is reduced (because the drops are more dispersed in time). Then in a second step, to recover the MMD of 5 microns, the number of cycles can be increased resulting in a higher flow rate. Thus, by adjusting the period of the control signal, the flow rate can be adjusted while keeping the MMD of the droplets generally constant.

It will be appreciated that one of the other parameters that can be adjusted includes the voltage of the control signal.

It will also be appreciated that this adjustment can be performed the other way around—i.e. the number of cycles can be selected to achieve a required flow rate, and then other parameters of the control signal can be adjusted in order to modify the droplet size.

Figure 7:
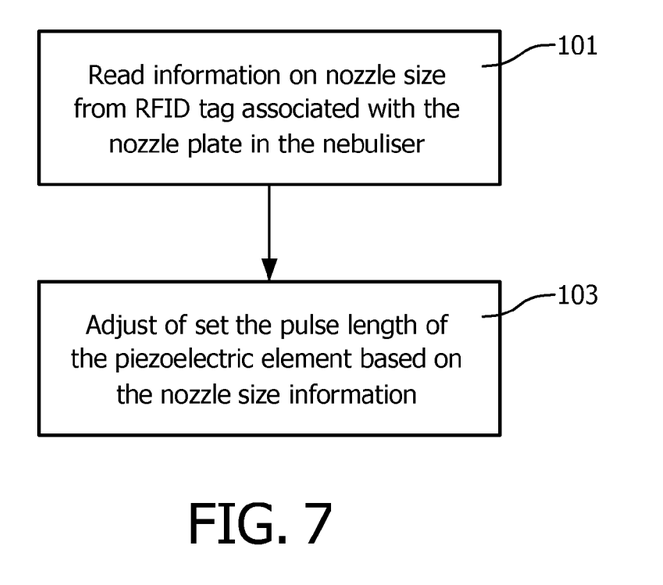
FIG. 7 is a flow chart illustrating a method of operating a nebulizer according to an embodiment of the invention.

A method of operating a nebulizer 2 according to the preferred embodiment of the invention is illustrated in FIG. 7. In the first step, step 101, which can occur when a nozzle plate 16 is first installed in a nebulizer 2 or when the nebulizer 2 is to be activated, the processor 18 activates the RFID tag reader 24 in order to read the information or indication on the average nozzle size stored in the RFID tag 22 in the nozzle plate 16.

Once the information or indication of the average nozzle size has been read from the nozzle plate 16, the processor 18 can process the information to determine the number of cycles in a pulse at which to operate the actuator (piezoelectric element) 14 in order to obtain the required flow rate and/or droplet size. In particular, a look-up table listing the number of cycles for different nozzle sizes can be stored in the memory 20, and the processor 18 can simply look-up the appropriate nozzle size, output rate and/or droplet size in the table and extract the required number of cycles. Alternatively the required number of cycles and other operating parameters could be stored on the RFID tag.

Once the required pulse length has been determined, the processor 18 can output an appropriate control signal to the actuator 14 which causes the actuator 14 to agitate the liquid 12 and to provide the droplets at the required output flow rate and/or droplet size (step 103).

Figure 4:
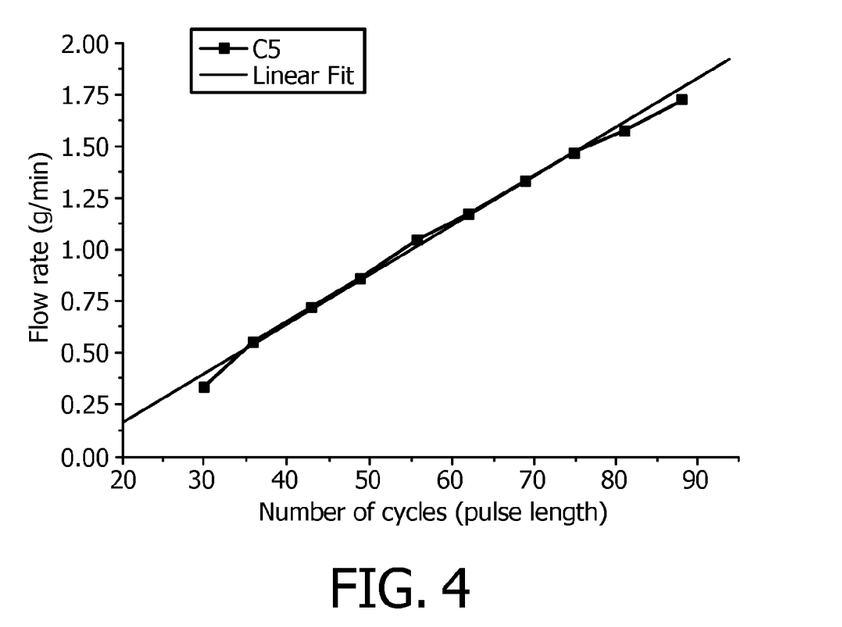
FIG. 4 is a graph illustrating the relationship between flow rate and the number of cycles in a pulse applied to a nozzle plate.
Figure 5:
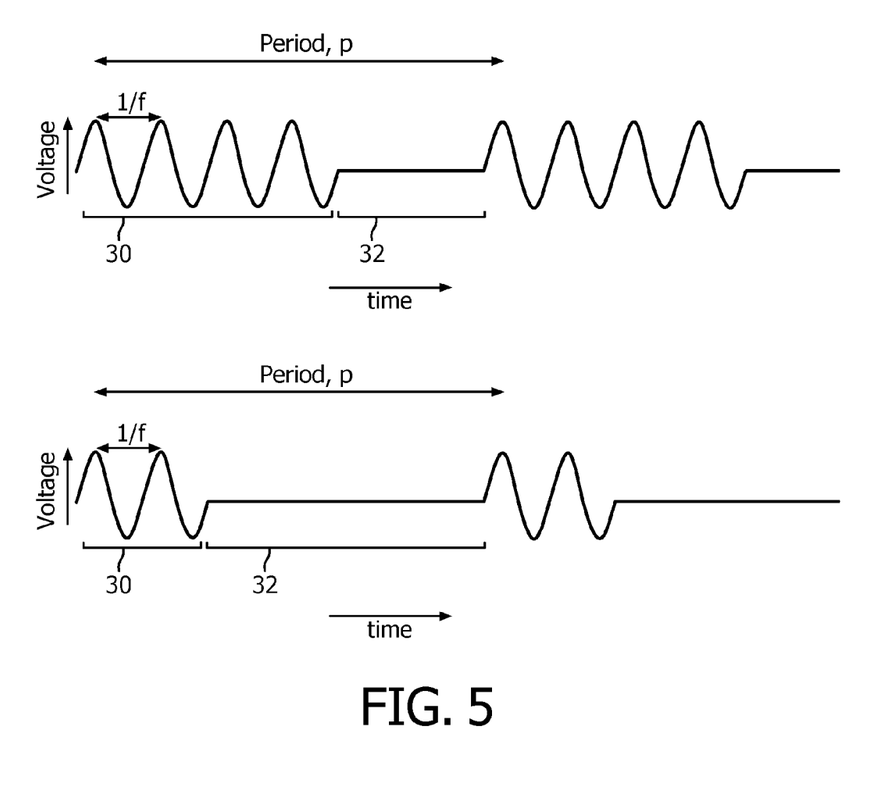
FIG. 5 is a diagram illustrating two exemplary signals for controlling an actuator in a nebulizer according to the invention.

If the nozzle plate 16 is removed from the nebulizer 2 and either cleaned and replaced, or replaced by another nozzle plate 16, the processor 18 can repeat the steps shown in FIG. 4 in order to operate the actuator 14 with the required pulse length.

Although in the preferred embodiment of the invention described above the control unit 17 is configured to control the nebulizer 2 such that the number of cycles in a pulse (i.e. the pulse length) for the actuator 14 is varied or set based on the size or average size of the nozzles in the nozzle plate 16, it will be appreciated that it is possible for other parameters defining the operation of the actuator 14 to be varied or set to achieve the required output rate and/or droplet size.

In particular, instead of (or even in addition to) varying the pulse length (number of cycles in a pulse) in the control signal, it is possible to achieve the required output rate and/or droplet size by adjusting (i) the amplitude (peak voltage) of the control signal (where the amplitude/voltage of the control signal determines the degree of actuation of the actuator 14 and where a higher voltage generally produces an increased output rate for a given nozzle plate 16), (ii) the period of the control signal (which would have the effect of reducing or increasing the length of the rest period relative to the active period), (iii) the frequency f of the cycles in the active portion 30, and/or (iv) adjusting the distance between the nozzle plate 16 and actuator 14.

Although in the illustrated embodiment the control signals output to the actuator 14 by the processor 18 cause the actuator 14 to operate in a 'pulsed' operation mode, it will be appreciated that it is possible to operate the actuator 14 in alternative modes of operation, including a continuous mode of operation (i.e. where there is no rest portion 32).

There is therefore provided an improved way of operating a nebulizer 2 to achieve a desired flow rate and/or droplet size, despite variations in nozzle size across different nozzle plates 16 that could be used in the nebulizer 2.

It will also be appreciated that, in addition to the control unit 17 and processor 18 described above, the invention can be provided in the form of a computer program carried on a computer readable medium that is configured to cause the processor 18 in the control unit 17 to execute the steps shown in FIG. 6. This program could be stored in memory 20.

Those skilled in the art will appreciate that the word "nebulizer" can be used interchangeably with the term drug delivery apparatus or atomizer, and the use of the word "nebulizer" is intended to cover forms and designs of nebulizer other than the specific type of nebulizer described above and illustrated in the Figures.

Furthermore, although the invention has been described in terms of a nebulizer that is primarily for use in administering a medicament, it will be appreciated that the invention can be applied to any other type of nebulizer or device in which a nozzle plate is actuated in order to nebulize a liquid, such as, for example an air humidifier, an electric shaver, a steam iron or a perfume dispenser.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A control unit for controlling the operation of a nebulizer, the nebulizer comprising a reservoir chamber for storing a liquid to be nebulized, an actuator, and a nebulizing element comprising a plurality of nozzles arranged to nebulize the liquid at a required output rate and/or with droplets of a required size upon operation of the actuator; wherein the control unit is configured to:
   obtain an indication of the size of the nozzles in the nebulizing element; and
   control the operation of the actuator based on the obtained indication of the size of the nozzles and based on the required output rate and/or with droplets of the required size, wherein controlling the operation of the actuator comprises adjusting one or more parameters of a control signal of the control unit.

2. A control unit as claimed in claim 1, wherein the control unit is configured to operate the actuator in a pulsed mode of operation in which the actuator is periodically operated at a frequency f for a number of cycles followed by a period of rest, and wherein the control unit is configured to operate the actuator at a first number of cycles when the nozzles are a first size and a second number of cycles when the nozzles are a second size, the second number of cycles being higher than the first number of cycles and the second size being less than the first size.

3. A control unit as claimed in claim 1, wherein the control unit is configured to adjust or set one or more operating parameters of the nebulizer based on the obtained indication to provide the nebulized liquid at the required output rate and/or with the required droplet size, the one or more operating parameters being selected from:
   the peak voltage of a control signal for the actuator;
   the length of an active portion and/or a rest portion of a periodic control signal for the actuator, the active portion of the control signal causing the actuator to operate to nebulize liquid;
   the frequency of a control signal for the actuator; and/or
   the distance between the actuator and the nebulizing element.

4. A control unit as claimed in claim 1, wherein the control unit comprises a reader for reading data stored in an electronically-readable tag associated with the nebulizing element, the data comprising the indication of the size of the nozzles in the nebulizing element.

5. A control unit as claimed in claim 1, wherein the control unit further comprises a memory that is configured to store a look-up table of nozzle sizes and values for at least one operating parameter for the actuator, and wherein the control unit is configured to use the look-up table and obtained indication to determine the value for the at least one operating parameter to use to operate the actuator and to provide the nebulized liquid at the required output rate and/or with the required droplet size.

* * * * *